United States Patent [19]
Karcher et al.

[11] Patent Number: 4,685,473
[45] Date of Patent: Aug. 11, 1987

[54] ORIENTABLE CARDIOVASCULAR SOUND

[75] Inventors: Gilles Karcher, Nancy; Max Amor, Vandoeuvre; Roger Niddam, Le Rancy; Jean-Pierre Villemot, Nancy, all of France

[73] Assignee: Medicorp Research Laboratories Corporation, Boca Raton, Fla.

[21] Appl. No.: 832,247

[22] Filed: Feb. 21, 1986

[30] Foreign Application Priority Data

Feb. 22, 1985 [FR] France ............................ 85 02568

[51] Int. Cl.⁴ .................................................. A61B 5/00
[52] U.S. Cl. ..................................... 128/772; 128/774; 604/95
[58] Field of Search ................... 128/10, 11, 657, 772, 128/773, 774; 604/95; 73/151

[56] References Cited

U.S. PATENT DOCUMENTS

| | | | |
|---|---|---|---|
| 3,665,928 | 5/1972 | Del Guercio | 604/95 |
| 3,773,034 | 11/1973 | Burns et al. | 604/95 |
| 4,150,676 | 4/1979 | Jackson | 128/657 |
| 4,403,985 | 9/1983 | Boretos | 604/95 |

Primary Examiner—Kyle L. Howell
Assistant Examiner—Randy Citrin
Attorney, Agent, or Firm—Darby & Darby

[57] ABSTRACT

Orientable endovascular sound for the exploration of the arteries. Between the head and the body, the sound has a zone of articulation, in which there are bellows which can be inflated by a fluid to produce the orientation of the head in a radial direction opposite the inflated bellows.

6 Claims, 4 Drawing Figures

ORIENTABLE CARDIOVASCULAR SOUND

FIELD OF THE INVENTION

The invention relates to an orientable endovascular sound.

BACKGROUND OF THE PRESENT INVENTION

For the exploration of the arteries, flexible sounds are often used, which are pushed from the outside along a metal guide. The form of these sounds and their flexibility are adapted to the vessels to be explored, but it remains generally difficult to move the sound past bends or forks.

One of the aims of the invention is to propose a sound whose end is orientable from the outside. Another aim of the invention is to provide, for this sound, means of orientation control which are particularly flexible.

Moreover, there are specialized sounds which have a particular form for the exploration of certain vessels such as the coronary arteries. Among these sounds there are, for example, the sounds of Judkins, Bourrassa, Amplatz, Cobra, etc. type. For each of these types of sound there is a family of five or six models adapting to the various sizes of the organs, for example, or to certain types of deformations of the organs. These families of sounds are characterized by a single general appearance but by different curvatures at the level of an elbow, for example.

Another aim of the invention is to reduce the number of models of sounds in each family by providing a single sound whose curvature can be modified from the outside to insure its adaptation to most of the clinical cases encountered.

SUMMARY OF THE INVENTION

The subject of the invention is an orientable endovascular sound comprising a sound body and a sound head, characterized in that, between the head and the body, the sound has a zone of articulation in which there is at least one bellows that can be inflated by a fluid to cause the orientation of the head in a radial direction opposite the inflated bellows.

According to other characteristics of the invention:
 (a) in the zone of articulation, the wall of the sound is extensible,
 (b) the bellows are supplied with fluid through channels lodged along the body of the sound,
 (c) the sound has two bellows placed on either side of the sound body to insure the orientation of the sound head in two opposite directions,
 (d) the sound has four bellows placed in pairs on either side of the sound body to insure the orientation of the sound head in four directions and in the bisectrices of these directions,
 (e) the sound has a curvature and comprises a single bellows disposed on the outside of the zone of curvature to vary this curvature.

Other characteristics will appear on reading the description which follows made with reference to the attached drawing.

DESCRIPTION OF THE PREFERRED EMBODIMENTS

Figure 1:
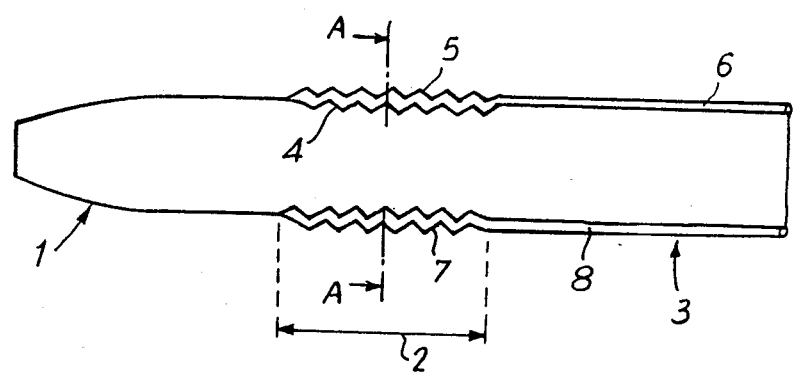
FIG. 1 shows a view in longitudinal section of an example of embodiment of an orientable sound according to the invention.
Figure 2:
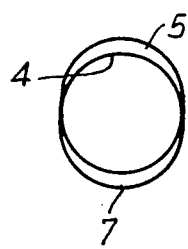
FIG. 2 shows a view in cross section along line A-A in FIG. 1.

Referring to FIG. 1 it can be seen that the endovascular sound has a head 1 of classic form and, between this head and the body 3 of the sound, a zone of articulation 2. In this zone 2 the wall 4 of the sound is extensible and outside this wall there is a bellows 5 which can be filled with fluid by means of a lateral channel 6 running the length of the sound. This bellows 5 (FIG. 2) extends over a certain width, which can be as much as half of the circumference of the sound. A bellows 7 symmetrical to the first relative to the horizontal axial plane, is supplied with fluid through a lateral channel 8.

When a sound is in a vessel and facing a fork, for example, head 1 can be oriented by injecting fluid into either of channels 6 or 8. Under the influence of the pressure of this fluid, the corresponding bellows, 5 or 7, respectively, inflates and extends, thereby causing the sound head 1 to tilt downward or upward, respectively.

Figure 3:
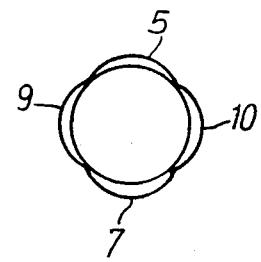
FIG. 3 shows a view in cross section of an example of embodiment of a sound orientable in several directions.

In the example of embodiment in FIG. 3, the sound is equipped, in addition to the two upper and lower bellows 5 and 7, with two other lateral bellows 9 and 10. When one of the bellows 9 or 10 is inflated by a fluid, the sound head 1 is oriented to the side opposite this bellows. It is thus possible to orient the head 1 in four directions by inflating just one of the four bellows at a time. It is also possible, by inflating two adjacent bellows such as 5 and 9 simultaneously, to orient the sound head in the direction comprised between bellows 7 and 10, that is to say to the left but at a 45° angle to the vertical, in the bisectrix of the directions of orientation corresponding to the two bellows.

Figure 4:
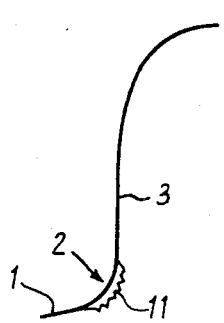
FIG. 4 is a schematic view in the mean axial plane of a sound of particular form whose curvature can be varied by controlling the inflation of a bellows according to the invention.

In the example of embodiment in FIG. 4, a sound of a special type, for example for the exploration of a coronary artery, has a head 1, a body 3 and between the two a zone of articulation 2 which is curved in the state of rest. Outside this zone of articulation, the sound has an inflatable belows 11. Depending on the degree of inflation of this bellows 11, the curvature of the sound is modified. It is thus possible to use only one model of sound and adapt it to the clinical case by simple adjustment of the inflation of the bellows. One advantage of this arrangement is that it permits a reduction in the time for studying coronary arteries, for example.

Thus, from the outside, and by simple injection of pressure into one or two of the lateral channels, the sound head can be given an orientation that facilitates its progression. The diameter and the position of the zone of articulation are determined as a function of the nature of the catheterization and of the arteries to be entered.

We claim:

1. An orientable, endovascular sound, comprising: a sound body; a sound head; and articulation means disposed between the sound head and the sound body, said means including at least one bellows for being inflated by a fluid to produce orientation of the head in a radial direction opposite the inflated belows, said articulation means being part of a continuous wall extending along said sound head and sound body.

2. A sound according to claim 1, wherein said articulation means includes a wall which is extensible.

3. A sound according to claim 1, wherein said bellows is supplied with fluid by a channel forming part of a wall of the body of the sound.

4. A sound according to claim 1, wherein said means includes two bellows placed on opposite portions of the sound body to insure orientation of the sound head in two opposite directions.

5. A sound according to claim 1, wherein said means includes four bellows placed in pairs on opposite portions of the sound body to insure orientation of the sound head in four directions and in the bisectrices of these directions.

6. A sound according to claim 1, wherein the sound body includes a curved portion and the articulation means includes a bellows disposed on the outside of the curved portion to vary the curvature of the curved portion.

* * * * *